(12) United States Patent
Jang et al.

(10) Patent No.: US 9,146,199 B2
(45) Date of Patent: Sep. 29, 2015

(54) X-RAY IMAGING APPARATUS AND METHOD

(75) Inventors: Kwang-eun Jang, Busan (KR); Jong-ha Lee, Hwaseong-si (KR); Kang-eui Lee, Yongin-si (KR); Young-hun Sung, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 538 days.

(21) Appl. No.: 13/552,976

(22) Filed: Jul. 19, 2012

(65) Prior Publication Data

US 2013/0022165 A1    Jan. 24, 2013

(30) Foreign Application Priority Data

Jul. 22, 2011    (KR) ........................ 10-2011-0073245

(51) Int. Cl.
*G01N 23/04* (2006.01)
*A61B 6/02* (2006.01)
*A61B 6/00* (2006.01)

(52) U.S. Cl.
CPC .............. *G01N 23/04* (2013.01); *A61B 6/025* (2013.01); *A61B 6/027* (2013.01); *A61B 6/482* (2013.01); *A61B 6/5205* (2013.01); *G01N 2223/419* (2013.01); *G01N 2223/6126* (2013.01)

(58) Field of Classification Search
USPC ..................................... 378/19, 62
See application file for complete search history.

(56) References Cited

U.S. PATENT DOCUMENTS 4,323,779 A * 4/1982 Albert .................. 378/98.6
2006/0269040 A1 11/2006 Mertelmeier

FOREIGN PATENT DOCUMENTS

| JP | 2008-79923 A | 4/2008 |
| JP | 2008-104673 A | 5/2008 |
| JP | 2010-233962 A | 10/2010 |
| KR | 10-2011-0055991 A | 5/2011 |
| KR | 10-1034258 B1 | 5/2011 |

OTHER PUBLICATIONS

Korean Office Action issued Mar. 28, 2014 in counterpart Korean Patent Application No. 10-2011-0073245. (8 pages including English translation).

Korean Office Action mailed Jul. 28, 2014 in counterpart Korean Application No. 10-2011-0073245 (5 pages, in Korean, including English translation).

* cited by examiner

*Primary Examiner* — Kiet T Nguyen
(74) *Attorney, Agent, or Firm* — NSIP Law

(57) ABSTRACT

An X-ray imaging apparatus and method is provided. An X-ray imaging apparatus includes an X-ray radiation unit configured to radiate a first X-ray and a second X-ray onto a target along a predetermined path, an X-ray detection unit configured to detect the radiated first X-ray and the second X-ray that have passed through the target, and an image data generation unit configured to generate cross-section data that respectively corresponds to the detected first X-ray and the detected second X-ray and represents a predetermined cross-sectional layer of the target. The first X-ray is radiated at a location on the predetermined path that is different from a location on the predetermined path at which the second X-ray is radiated, the first X-ray including X-ray spectra that are different from X-ray spectra of the second X-ray.

19 Claims, 9 Drawing Sheets

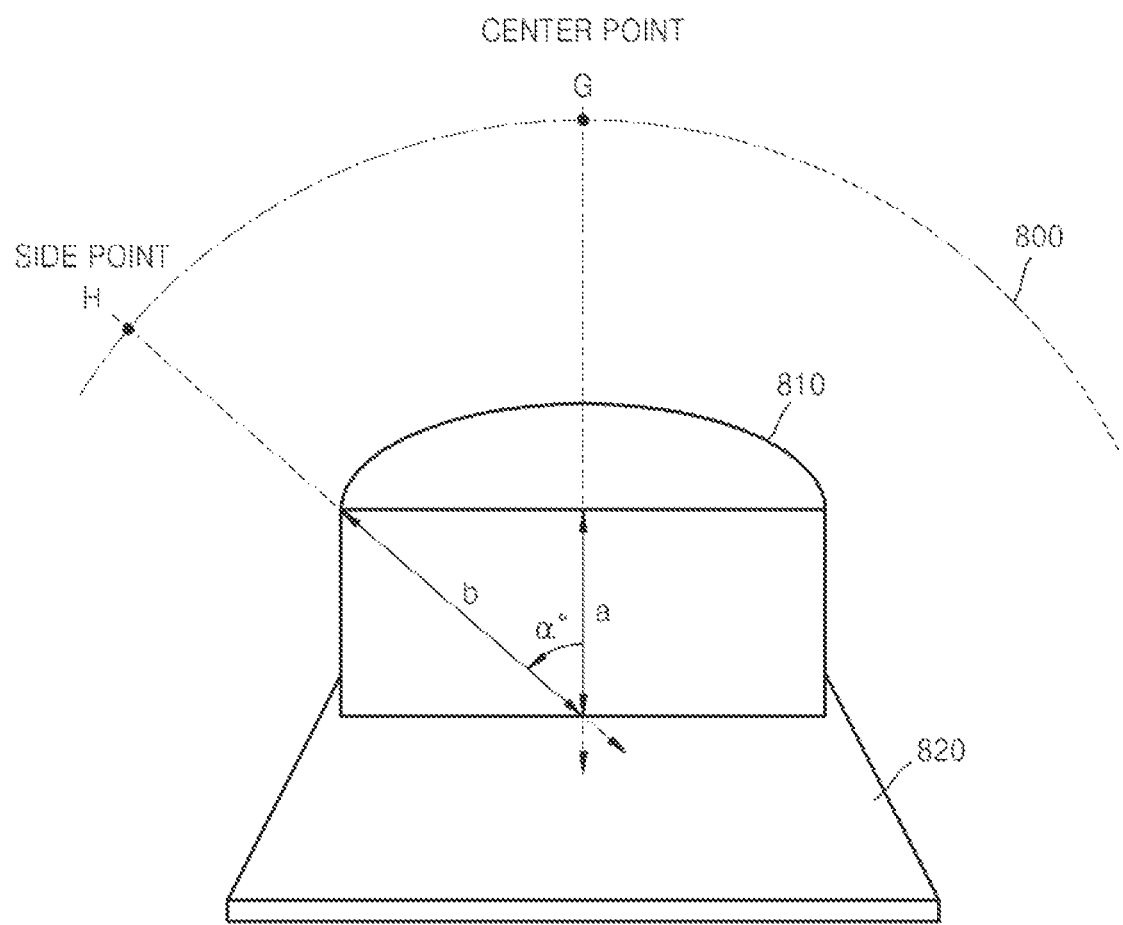

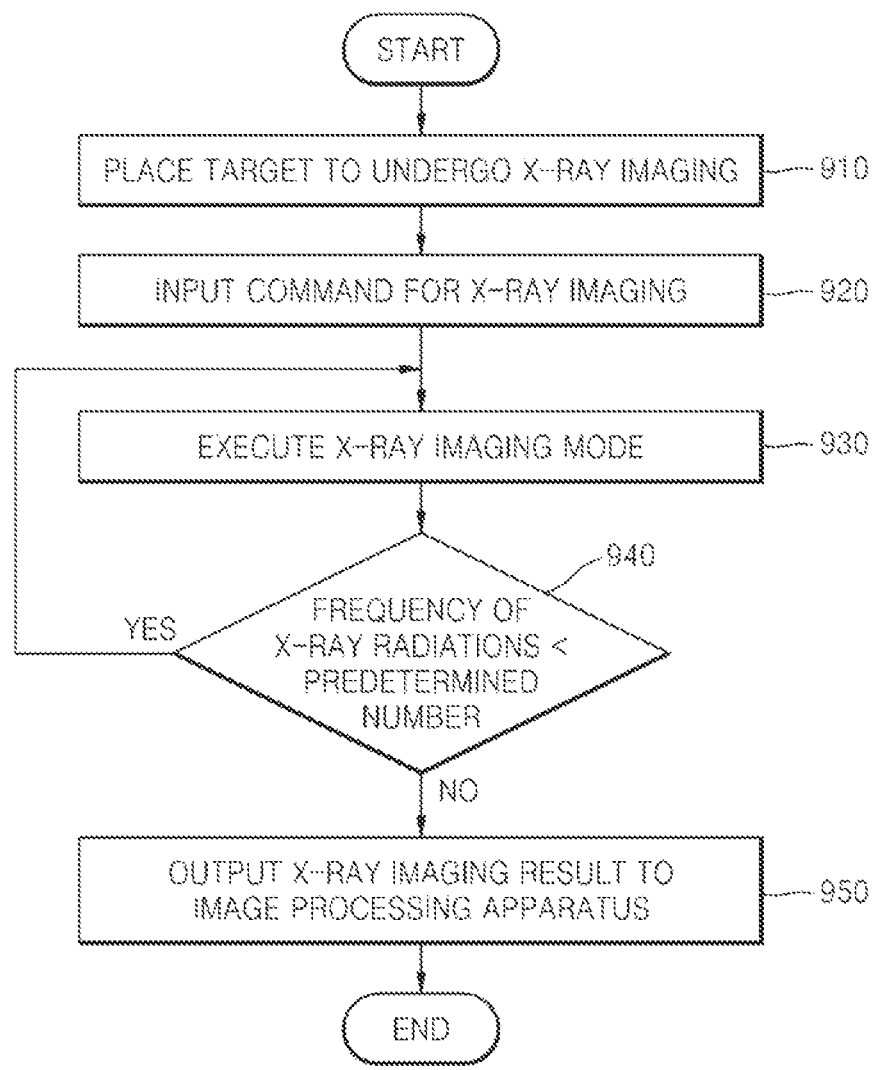

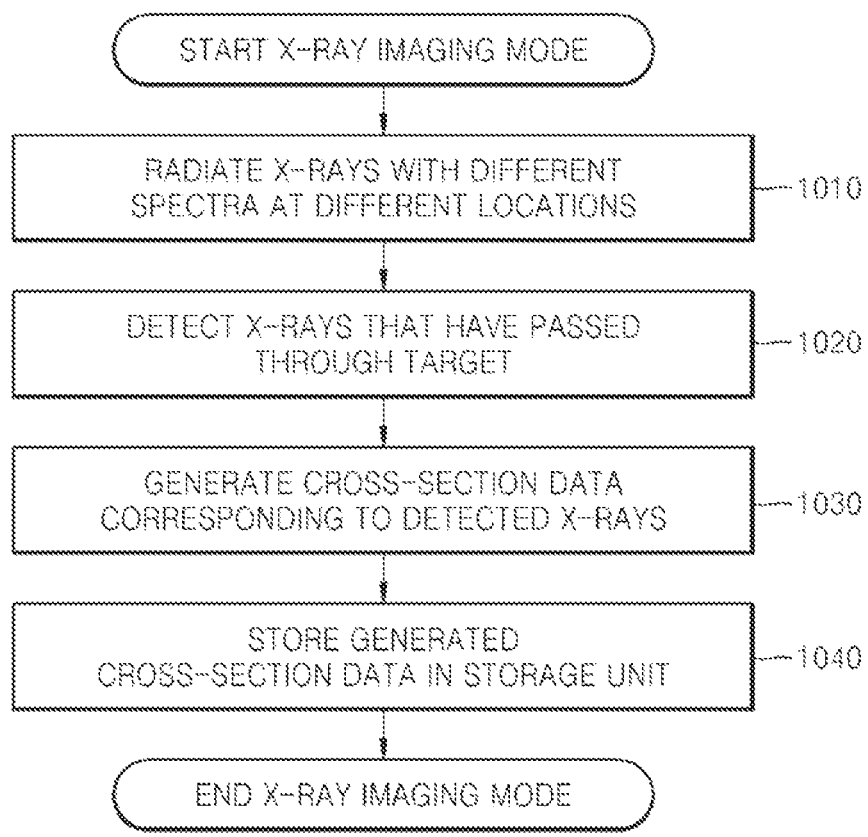

X-RAY IMAGING APPARATUS AND METHOD

CROSS-REFERENCE TO RELATED APPLICATIONS

This application claims the benefit under 35 U.S.C. §119(a) of Korean Patent Application No. 10-2011-0073245, filed on Jul. 22, 2011, in the Korean Intellectual Property Office, the entire disclosure of which is incorporated herein by reference for all purposes.

BACKGROUND

1. Field

The following description relates to an X-ray imaging apparatus and method.

2. Description of Related Art

X-ray mammography is a type of photographic technology used to test tissues in diagnostic targets. A type of X-ray mammography, referred to as full field digital mammography (FFDM), has the ability to detect very small microcalcifications in tissue. Mammography lacks depth information in an X-ray scanning direction. As a result, tissues of a diagnostic target appear to overlap in images produced through mammography.

Unlike mammography, computed tomography (CT) involves acquiring tomograms of a target by scanning with X-rays about the target at 180 degrees and reconstructing the tomograms to generate an image representing the target. Tomosynthesis also involves acquiring tomograms of a target by scanning the target with X-rays and reconstructing the tomograms to generate an image representing the target.

However, due to physical characteristics inherent in X-rays, a specific spectrum of X-rays has a predefined penetration distance in a target, and, thus, may be hard to be detected if radiated beyond a predefined penetration distance. The X-ray scanning of the target in tomosynthesis is within a range of angles that is relatively limited in comparison with CT. In other words, tomosynthesis results in a reduced amount of acquired tomograms and a target having a reduced exposure to X-rays in comparison with CT.

SUMMARY

In one general aspect, an X-ray imaging apparatus includes an X-ray radiation unit configured to radiate a first X-ray and a second X-ray onto a target along a predetermined path, an X-ray detection unit configured to detect the radiated first X-ray and the second X-ray that have passed through the target, and an image data generation unit configured to generate cross-section data that respectively corresponds to the detected first X-ray and the detected second X-ray and represents a predetermined cross-sectional layer of the target. The first X-ray is radiated at a location on the predetermined path that is different from a location on the predetermined path at which the second X-ray is radiated, the first X-ray including X-ray spectra that are different from X-ray spectra of the second X-ray.

The X-ray imaging apparatus may include that the X-ray spectra of the first X-ray and the X-ray spectra of the second X-ray are respectively dependent on the locations in which the first X-ray and the second X-ray are radiated by the X-ray radiation unit.

The X-ray imaging apparatus may include that the X-ray radiation unit includes an X-ray generation unit and an arrayed mask, the X-ray generation unit being configured to radiate the first X-ray and the second X-ray onto the target, the arrayed mask being on an X-ray emitting side of the X-ray generation unit, the arrayed mask including masks that are removable based on a site at which the target is disposed and the locations at which the first X-ray and the second X-ray are disposed.

The X-ray imaging apparatus may include that the X-ray radiation unit is further configured to radiate one or more spectra of X-rays at a location on the predetermined path that is different from a location on the predetermined path at which the first X-ray and the second X-ray are radiated, the one or more spectra being different from the spectra of the first X-ray and the second X-ray.

The X-ray imaging apparatus may include that the first X-ray has an energy spectrum that is greater than an energy spectrum of the second X-ray when the location at which the first X-ray is radiated is farther away from a center of the predetermined path than the location at which the second X-ray is radiated, and the energy spectrum of the second X-ray is greater than the energy spectrum of the first X-ray when the location at which the second X-ray is radiated is farther away from the center of the predetermined path than the location at which the first X-ray is radiated.

The X-ray imaging apparatus may include that the first X-ray and the second X-ray are alternately radiated at different locations on the predetermined path.

The X-ray imaging apparatus may include that, when multiple pieces of cross-section data are generated based on multiple radiations of X-rays by the X-ray radiation unit in multiple locations, the image data generation unit is further configured to generate three-dimensional (3D) volume data representing the target in three dimensions by cumulating the generated multiple pieces of cross-section data.

The X-ray imaging apparatus may include a storage unit configured to store the generated cross-section data.

The X-ray imaging apparatus may include that the X-ray imaging apparatus is used in tomosynthesis.

In another general aspect, an X-ray imaging method includes radiating a first X-ray and a second X-ray onto a target along a predetermined path, detecting the radiated first X-ray and the radiated second X-ray that have passed through the target, and generating cross-section data that respectively corresponds to the detected first X-ray and the detected second X-ray and represents a predetermined cross-sectional layer of the target. The first X-ray is radiated at a location on the predetermined path that is different from a location on the predetermined path at which the second X-ray is radiated, the first X-ray including X-ray spectra that are different from X-ray spectra of the second X-ray.

The method may include that the X-ray spectra of the first X-ray and the X-ray spectra of the second X-ray are respectively dependent on the locations in which the first X-ray and the second X-ray are radiated.

The method may include that the radiating of the first X-ray and the second X-ray includes radiating one or more spectra of X-rays at a location on the predetermined path that is different from a location on the predetermined path at which the first X-ray and the second X-ray are radiated, the one or more spectra being different from the spectra of the first X-ray and the second X-ray.

The method may include that the first X-ray has an energy spectrum that is greater than an energy spectrum of the second X-ray when the location at which the first X-ray is radiated is farther away from a center of the predetermined path than the location at which the second X-ray is radiated, and the energy spectrum of the second X-ray is greater than the energy spectrum of the first X-ray when the location at which the second X-ray is radiated is farther away from the center of the predetermined path than the location at which the first X-ray is radiated.

The method may include that the first X-ray and the second X-ray are alternately radiated at different locations on the predetermined path.

The method may include, when multiple pieces of cross-section data are generated based on multiple radiations of X-rays in multiple locations, generating three-dimensional (3D) volume data representing the target in three dimensions by cumulating the generated multiple pieces of cross-section data.

The method may include storing the generated cross-section data.

The method may include that the X-ray imaging method is used in tomosynthesis.

In yet another general aspect, there is provided a non-transitory computer readable recording medium having recorded thereon a program for executing an X-ray imaging method.

In still another general aspect, an X-ray imaging apparatus includes an X-ray radiation unit configured to radiate X-rays onto a target from one or more locations along a predetermined path, each of the radiated X-rays including a respective X-ray spectra corresponding to the locations, respectively, an X-ray detection unit configured to detect a plurality of the radiated X-rays that have passed through the target, an image data generation unit configured to generate pieces of cross-section data and three-dimensional (3D) volume data, the 3D volume data being configured to represent the target in three dimensions, the pieces respectively corresponding to the detected plurality of the radiated X-rays and representing predetermined cross-sectional layers of the target, the pieces being configured to cumulatively represent the target in three dimensions as the 3D volume data.

Other features and aspects may be apparent from the following detailed description, the drawings, and the claims.

BRIEF DESCRIPTION OF THE DRAWINGS

FIG. 8 is a diagram illustrating an example of variations in X-ray penetration distance in a target when the X-ray radiation unit of FIG. 5 is located at center and side points on an arc path.

FIG. 9 is a flowchart illustrating an example of an X-ray imaging method.

FIG. 10 is a detailed flowchart illustrating an example of an X-ray imaging mode, which corresponds to the performing of the X-ray imaging mode recited with respect to FIG. 9.

Figure 1:
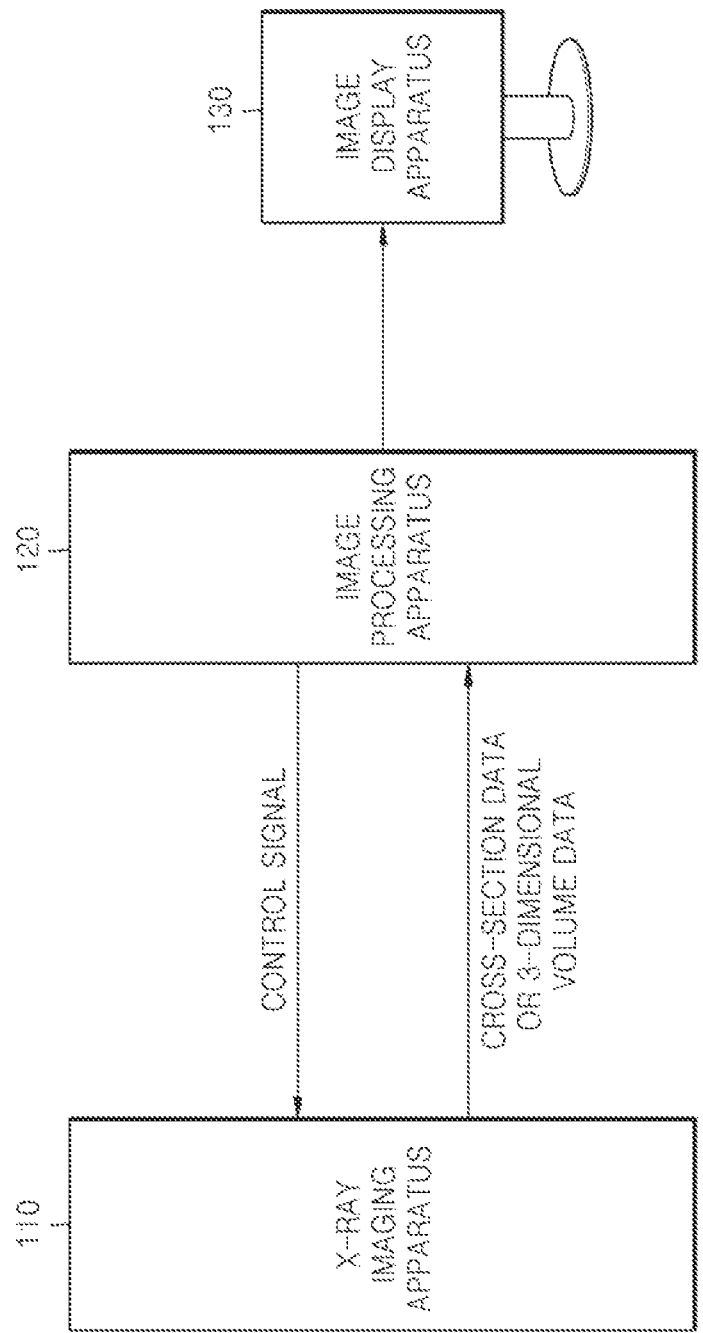
FIG. 1 is a schematic diagram illustrating an example of an X-ray diagnosis system.

Throughout the drawings and the detailed description, unless otherwise described, the same drawing reference numerals will be understood to refer to the same elements, features, and structures. The relative size and depiction of these elements may be exaggerated for clarity, illustration, and convenience.

DETAILED DESCRIPTION

The following detailed description is provided to assist the reader in gaining a comprehensive understanding of the methods, apparatuses, and/or systems described herein. Accordingly, various changes, modifications, and equivalents of the systems, apparatuses and/or methods described herein will be suggested to those of ordinary skill in the art. Also, descriptions of well-known functions and constructions may be omitted for increased clarity and conciseness.

FIG. 1 is a schematic diagram illustrating an example of an X-ray diagnosis system. Referring to the example illustrated in FIG. 1, the X-ray diagnosis system includes an X-ray imaging apparatus 110, an image processing apparatus 120, and an image display apparatus 130.

In an example, the X-ray imaging apparatus 110 includes an X-ray radiation unit (not shown) and an X-ray detection unit (not shown). In this example, the X-ray radiation unit radiates X-rays onto a target for which a diagnosis is desired. The target may be a breast, a chest, or any other part of a body known to one of ordinary skill in the art to be commonly subjected to X-rays for diagnosis purposes.

The X-ray detection unit detects an X-ray that has passed through the target and generates an electric signal based on the detected X-ray. Upon receipt of an instruction from a doctor or any other type of medical expert known to one of ordinary skill in the art, the X-ray radiation unit radiates an X-ray toward the target. The X-ray detection unit detects the radiated X-ray that has passed through the target and generates an electric signal from the detected X-ray. Only radiated X-rays that have passed through the target for a short period of time are detected by the X-ray detection unit. Specific cross-sectional information of the target may be determined based on the location at which the X-rays are detected. The electric signal generated by the X-ray detection unit is converted into cross-section data representing a cross-sectional layer of the target. Through multiple radiations of X-rays, multiple pieces of cross-section data may be generated. Three-dimensional (3D) volume data may be generated by cumulating adjacent pieces of the cross-section data. The generated cross-section data or the 3D volume data is transferred to the image processing apparatus 120.

The image processing apparatus 120 receives the cross-section data or the 3D volume data transferred from the X-ray imaging apparatus 110. The image processing apparatus 120 generates an image, which is to be displayed on the image display apparatus 130, based on the cross-section data or the 3D volume data. 3D volume data refers to data representing a target in three dimensions by cumulating multiple pieces of cross-section data. In an example, the image processing apparatus 120 generates a tomogram representing a cross-sectional layer of the target from the cross-section data. The image display apparatus 130 displays the image generated and transferred from the image processing apparatus 120.

In this example, assuming that there are cross-sectional layers in multiple directions crossing over the 3D volume data, tomograms are generated from data of each cross-sectional layer and are reconstructed to generate a 3D image representing the target. To generate tomograms from cross-section data, any process known to one of ordinary skill in the art, such as soft tissue correction, may be followed by restoration using an algorithm such as filtered back projection or maximum likelihood-expectation maximization. In an example, a tomogram may be generated from cross-section data generated from one or more spectra of X-rays based on a restoration algorithm known to one of ordinary skill in the art.

Figure 2:
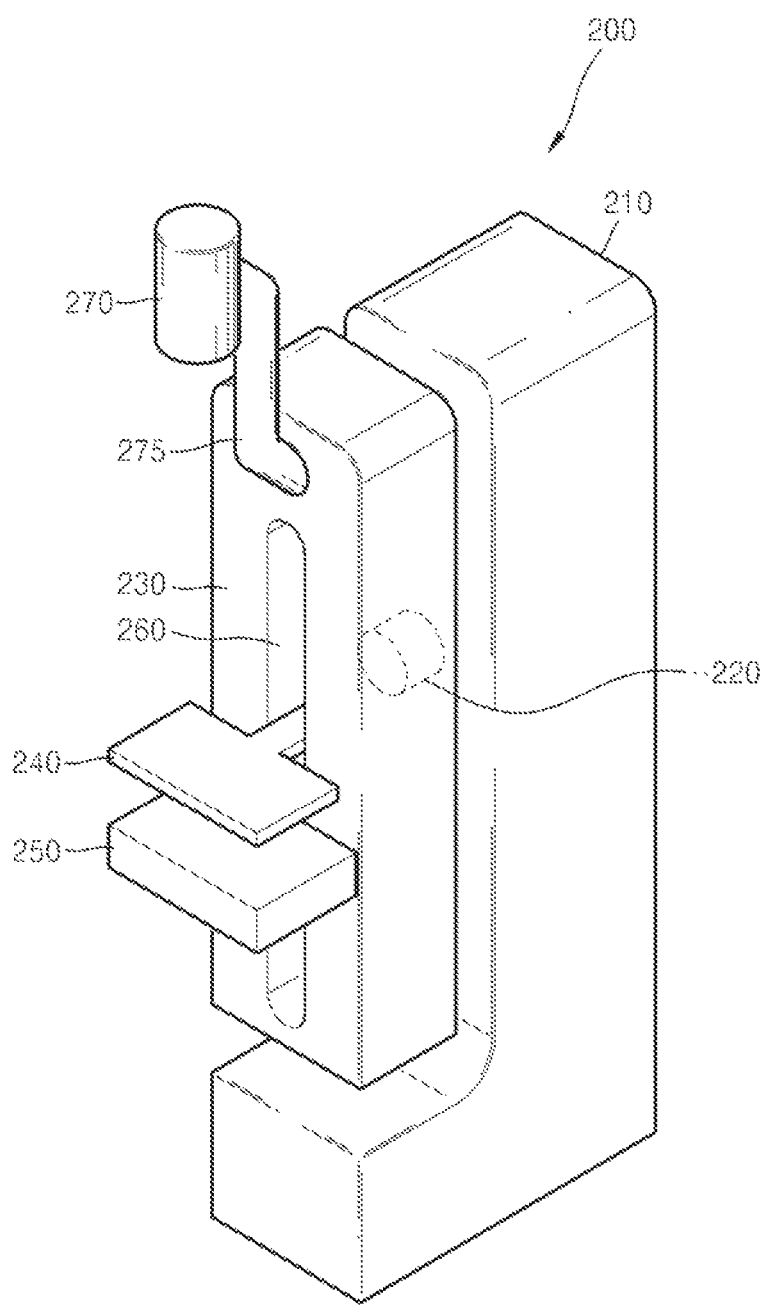
FIG. 2 is a perspective external diagram illustrating an example of an X-ray imaging apparatus of FIG. 1.

FIG. 2 is a perspective external diagram illustrating an example of an X-ray imaging apparatus of FIG. 1. Referring to the example illustrated in FIG. 2, the X-ray imaging apparatus 200 includes a support 210, a rotation unit 220, a body unit 230, a press unit 240, an X-ray detection unit 250, a guide groove unit 260, and an X-ray radiation unit 270. The support unit 210, which is connected to the body unit 230 by the rotation unit 220, supports the components of the X-ray imaging apparatus 200. The rotation unit 220, which is located between the support unit 210 and the body unit 230, turns the body unit 230 clockwise or counterclockwise. The body unit 230 is connected to the press unit 240, the X-ray detection unit 250, and the X-ray radiation unit 270. The guide groove unit 260 is formed in the body unit 230. The press unit 240 fixes a target (not shown), which may be disposed between the press unit 240 and the X-ray detection unit 250, so that it does not move by appropriately adjusting a spacing with respect to the X-ray detection unit 250. In an example, the press unit 240 and the X-ray detection unit 250 are both movable along the guide groove unit 260. The X-ray radiation unit 270, which is connected to the body unit 230 by the connection member 275, radiates X-rays onto the target.

Figure 3:
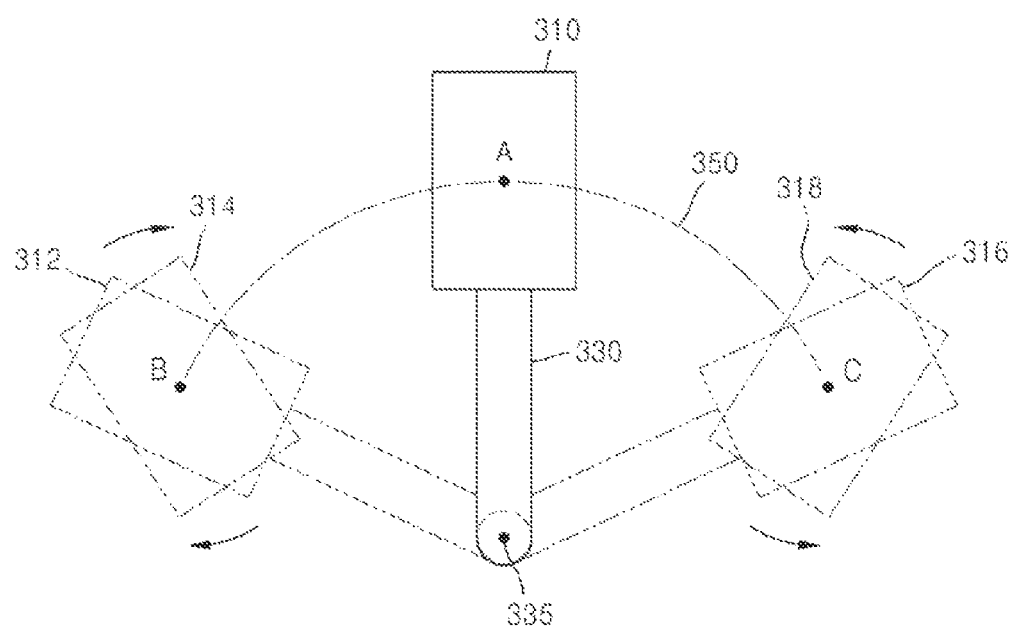
FIG. 3 is a diagram illustrating an example of location shifts of an X-ray radiation unit by rotation of a connection member connected to the X-ray radiation unit and rotation of the X-ray radiation unit about its own axis.

FIG. 3 is a diagram illustrating an example of location shifts of an X-ray radiation unit 310 by rotation of a connection member 330 connected to the X-ray radiation unit and rotation of the X-ray radiation unit 310 about its own axis. In this example, the connection member 330 connects the X-ray radiation unit 310 to a body unit (not shown), and may be rotatable clockwise or counterclockwise independent from the body unit. Referring to the example illustrated in FIG. 3, if the connection member 330 turns about a rotary shaft 335 counterclockwise by a predetermined angle with the X-ray radiation unit 310 being at a location A, the X-ray radiation unit 310 is moved toward a location B. On the contrary, if the connection member 330 turns about the rotary shaft 335 clockwise by a predetermined angle, the X-ray radiation unit 310 is moved toward a location C. The points A, B, and C form an arc path 350 when connected to one another. If the connection member 330 is rotated by a predetermined angle, the location of the X-ray radiation unit 310 connected to the connection member 330 shifts, drawing an arc path 350 by an equal angle to that by which the connection member 330 is turned.

In this example, as the location of the X-ray radiation unit 310 shifts, the path that the center of the moving X-ray radiation unit 310 draws is an arc as described above. However, that path that the center of the moving X-ray radiation unit draws is not limited thereto and, in other examples, is a circle or a line. For the purposes of description and explanation, in this example, the location of the X-ray radiation unit 310 is shifted within a predefined range to draw an arc.

In this example, the X-ray radiation unit 310 is connected to the connection member 330, and is rotatable clockwise or counterclockwise independent from the connection member 330. For example, the X-ray radiation unit 310 at location B may be selectively turned clockwise from a location 312 to a location 314 independent of the connection member 330. The X-ray radiation unit 310 at location C may be selectively turned counterclockwise from a location 316 to a location 318 independent of the connection member 330. The rotation of the connection member 330 connected to the X-ray radiation unit 310 and the rotation of the X-ray radiation unit 310 on its axis shifts the location of the X-ray radiation unit 310 to enable a radiation of X-rays onto a target in an appropriate direction.

Figure 4:
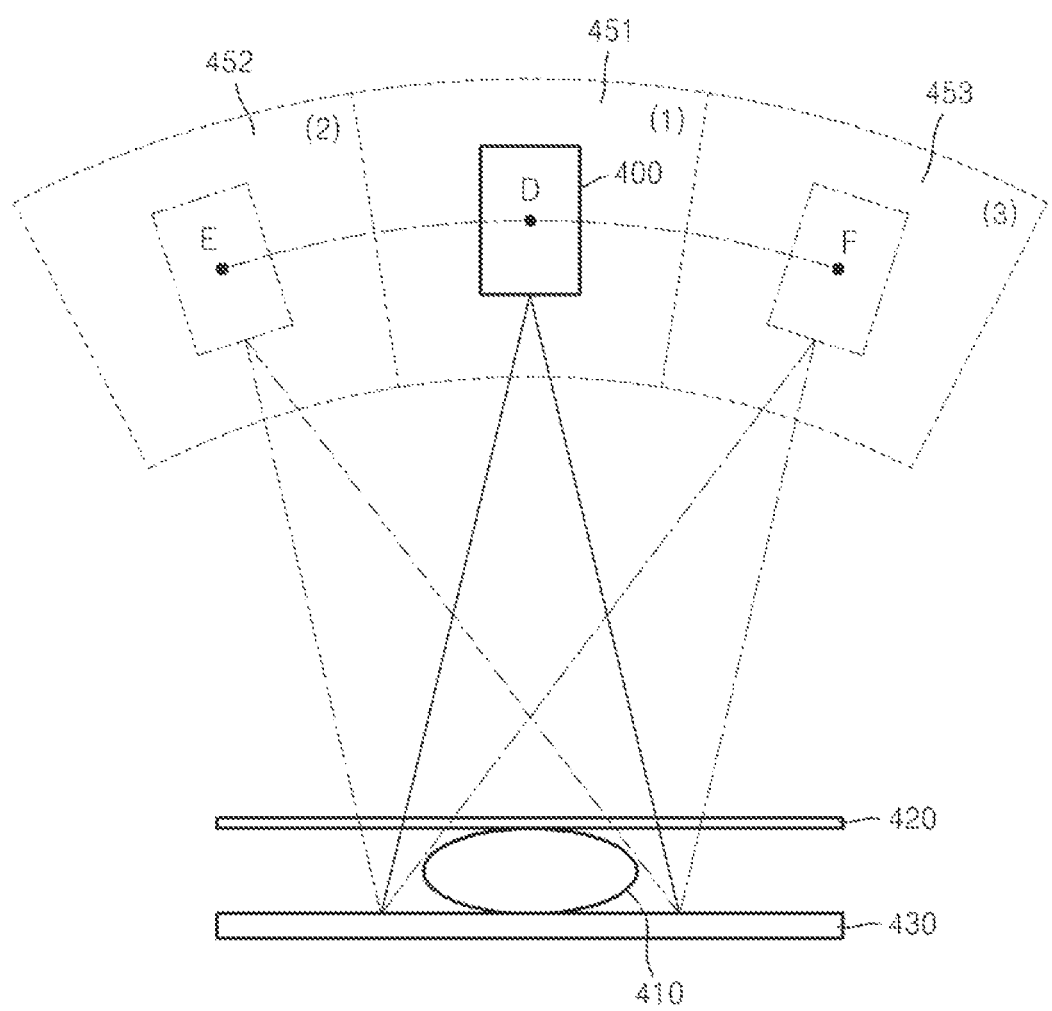
FIG. 4 is a diagram illustrating an example of X-ray radiations of an X-ray radiation unit at different locations.

FIG. 4 is a diagram illustrating an example of X-ray radiations of an X-ray radiation unit 400 at different locations. These locations include, but are not limited to, the location D, the location E, and the location F illustrated in FIG. 4. A target 410 is disposed between a press unit 420 and an X-ray detection unit 430 to be unmovable by being pressed, and is held by the press unit 420. Afterward, the X-ray radiation unit 400 radiates X-rays at the locations D, E, and F.

In an example, the X-ray radiation unit 400 radiates X-rays having different X-ray spectra at the different locations D, E and F. X-ray spectra refer to a distribution of X-ray intensities with respect to wavelengths. X-rays may produce either continuous X-ray spectra or characteristic X-ray spectra. Continuous X-ray spectra consist of continuous wavelengths of X-rays emitted, as a kind of safe radiation, upon a sudden stop of accelerating electrons emanating from a negative electrode due to a bombarding by the accelerating electrons of a positive electrode. Characteristic X-ray spectra are generated by energy that is emitted when an electron fills an empty site of an atom in a positive electrode from which an electron revolving in an orbit was lost when exposed to high energy.

Thus, in this example, a change of an element constituting the positive electrode, which is a target for accelerating electrons to bombard, enables acquisition of a different spectrum of X-rays with an equal voltage level. An application of a high voltage without such a change of the element of the positive electrode enables accelerating electrons to be rapidly bombarded by the positive electrode to attain a different spectrum of X-rays. In other words, X-rays having heterogeneous spectra are generated by changing a voltage level applied between the positive and negative electrodes of an X-ray tube or changing the material constituting the positive electrode.

In an example, the X-ray radiation unit 400 includes a parameter adjustment unit (not shown) that is used in generating heterogeneous spectra. If a parameter to generate heterogeneous spectra of X-rays is the voltage applied between the positive and negative electrodes, the parameter adjustment unit has a configuration that is the same as a configuration of a voltage adjustment unit that adjusts the level of a voltage applied to the X-ray tube. In another example, if the parameter to generate heterogeneous spectra of X-rays is the material of the positive electrode hit by accelerating electrons, the parameter adjustment unit has a configuration that is the same as a configuration of a target changing unit that changes the positive electrode with one made of a different material to serve as the target. If the X-ray radiation unit 400 includes one or more positive electrodes made of different materials, the target changing unit places one of the positive electrodes at a location that is to be bombarded by accelerating electrons to enable generation of heterogeneous spectra of X-rays. In an example, the positive electrodes are partitioned off by forming a rotary unit. In this case, the target changing unit is a rotation adjustment member that adjusts a rotation angle of the rotary unit.

In some examples, X-rays of heterogeneous spectra are radiated based on the location of the X-ray radiation unit 400. In addition, X-rays of homogeneous spectra are radiated if the location of the X-ray radiation unit 400 is limited within a region. In other words, the X-ray radiation unit 400 radiates X-rays of homogeneous several times within a region. Referring to the example illustrated in FIG. 4, when the center of the X-ray radiation unit 400 is in any location within a region (1) 451, the X-ray radiation unit 400 radiates X-rays of homogeneous spectra with respect to those radiated by the X-ray radiation unit 400 at the location D. When the center of the X-ray radiation unit 400 is at any location within a region (2) 452, the X-ray radiation unit 400 radiates X-rays of homogeneous spectra with respect to those radiated by the X-ray radiation unit 400 at the location E. When the center of the X-ray radiation unit 400 is at any location within a region (3) 453, the X-ray radiation unit 400 radiates X-rays of homogeneous spectra with respect to those radiated by the X-ray radiation unit 400 at the location F.

In other examples, the region in which the X-ray radiation unit 400 is located is defined to be smaller or larger than in the previously described examples. In these examples, the X-ray radiation unit 400 radiates X-rays of different spectra whenever shifted to another region.

In another example, the X-ray radiation unit 400 alternately radiates X-rays of different spectra whenever being shifted to another region. For example, assuming that the region in which the X-ray radiation unit 400 is located is divided into six sequential sub-regions (1) to (6), the X-ray radiation unit 400 may radiate a first spectrum of X-rays when shifted into the sub-regions (1), (3), and (5) and a second spectrum of X-rays when shifted into the sub-region (2), (4), and (6). If intended to generate three heterogeneous spectra of X-rays, the X-ray radiation unit 400 may radiate a first spectrum of X-rays in the sub-regions (1) and (4), a second spectrum of X-rays in the sub-regions (2) and (5), and a third spectrum of X-rays in the sub-regions (3) and (6). When the region in which the X-ray radiation unit 400 is located is further divided into more sub-regions, the X-ray radiation unit may alternately radiate spectra of X-rays of greater diversity.

Figure 5:
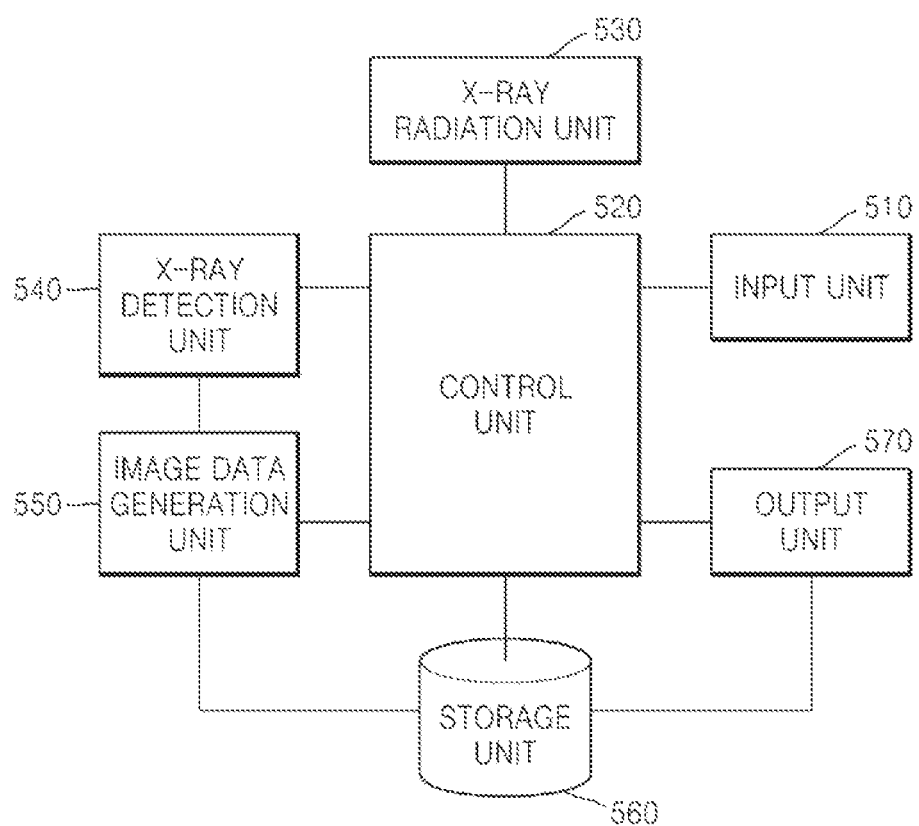
FIG. 5 is a block diagram illustrating an example of an X-ray imaging apparatus of FIG. 1.

FIG. 5 is a block diagram illustrating an example of an X-ray imaging apparatus 110 of FIG. 1. Referring to the example illustrated in FIG. 5, the X-ray imaging apparatus 110 of FIG. 1 includes an input unit 510, a control unit 520, an X-ray radiation unit 530, an X-ray detection unit 540, an image data generation unit 550, a storage unit 560, and an output unit 570. The input unit 510 receives a command from a user to capture images based on X-rays. An example of the user is a medical expert or any other individual or entity known to one of ordinary skill in the art to issue commands regarding the capturing of X-ray images. The input unit 510 receives any command known to one of ordinary skill in the art to control the X-ray imaging apparatus 110, such as, for example, a command to shift the location of the X-ray radiation unit 530, a command to radiate X-rays, a command to adjust a parameter to generate heterogeneous spectra of X-rays, a command to rotate the body of the X-ray imaging apparatus 110 or the X-ray radiation unit 530, or a command to move the press unit 240 (see FIG. 2) or the X-ray detection unit 540. Information about all the commands received from the user is transferred to the control unit 520. The control unit 520 controls the elements of the X-ray imaging apparatus 110 according to user commands.

The X-ray radiation unit 530 receives all commands relating to X-ray radiation from the control unit 520. After being moved to a location designated by the user, which is one of the locations linked together to form a predetermined path, the X-ray radiation unit 530 radiates X rays of an appropriate spectrum onto the target. Taking a target dose of X-rays to be radiated onto the target into account, the X-ray radiation unit 530 radiates X-rays at an appropriate frequency of radiation and an appropriate dose per radiation.

The X-ray detection unit 540 detects X-rays that have passed through the target. After the X-rays radiated by the X-ray radiation unit 530 pass through the target, the X-rays that have passed through the target are detected by the X-ray detection unit 540. In an example, the X-ray detection unit 540 includes a set of cells. An X-ray signal detected in the cells is converted to an electric signal. As an example, the X-ray detection unit 540 may be a flat panel detector.

The image data generation unit 550 receives the electric signal corresponding to the X-rays detected by the X-ray detection unit 540 and generates digital data of information about a cross-section of the target from the received electric signal, which hereinafter will be referred to as "cross-section data". One piece of cross-section data, which includes information about a cross-sectional layer of the target, is generated from a signal radiation of X-rays. In an example, when the X-ray radiation unit 530 radiates X-rays several times while being moved to different locations, the X-ray detection unit 540 generates multiple pieces of cross-section data of different cross-sectional layers of the target. 3D volume data representing the target in three dimensions may be generated by cumulating adjacent cross-section data from the multiple pieces of cross-section data.

The storage unit 560 stores the cross-section data generated by the image data generation unit 550. In another example, the storage unit 560 also stores the 3D volume data generated by the image data generation unit 550. The storage unit 560 transfers the cross-section data or the 3D volume data to the output unit 570 upon request of the user.

Figure 6:
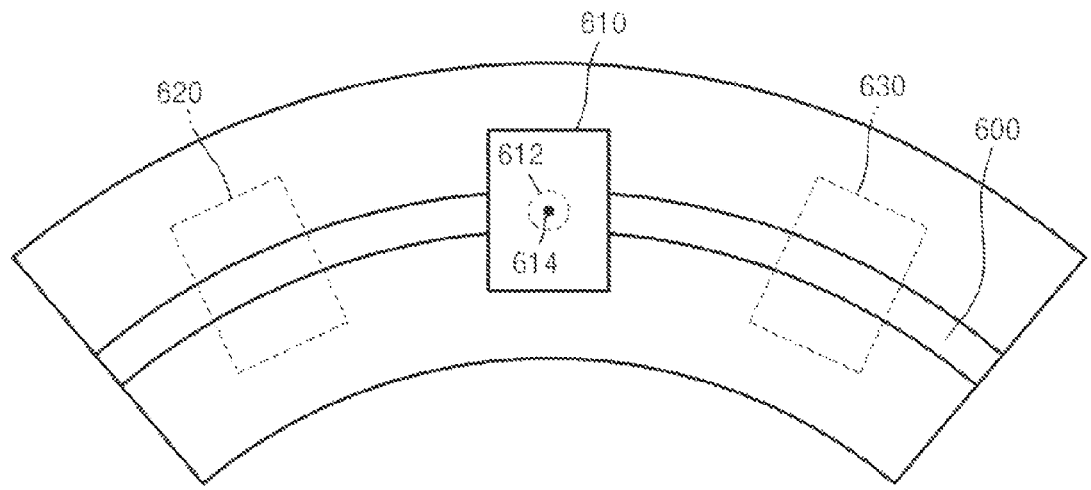
FIG. 6 is a diagram illustrating an example of X-ray radiation by an X-ray radiation unit.

The X-ray radiation unit 530 may radiate X-rays, for example, while being connected to the connection member 275 as illustrated in FIG. 2, while being formed as illustrated in FIGS. 6 and 7, or in other ways known to one of ordinary skill in the art.

FIG. 6 is a diagram illustrating an example of X-ray radiation by an X-ray radiation unit 610. In an example, the X-ray radiation unit 610 is able to horizontally slide along a guide groove 600, which may be previously established, so as not to be connected to the rotary connection member 275, as illustrated in FIG. 2. In other words, the X-ray radiation unit 610 is moved left to a location 620 or is moved in the opposite direction, i.e., right, to a location 630. The X-ray radiation unit 610 is connected to a connection unit 612, which is able to slide along the guide groove 600, to rotate about its own axis independent of the connection unit 612. The X-ray radiation unit 610 radiates heterogeneous spectra of X-rays according to the location thereof. In another example, the X-ray radiation unit 610 radiates a homogeneous spectrum of X-rays several times within the predefined region.

Figure 7A:
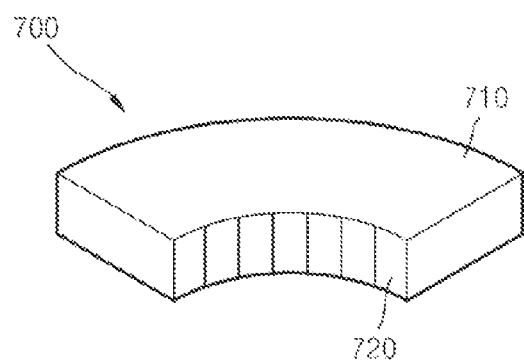
FIGS. 7A and 7B are diagrams illustrating another example of X-ray radiation by an X-ray radiation unit.
Figure 7B:
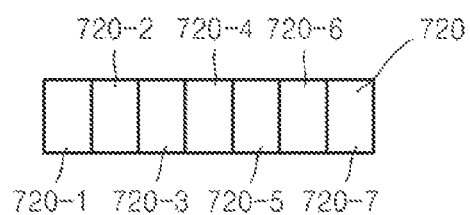

FIGS. 7A and 7B are diagrams illustrating an example of X-ray radiation by an X-ray radiation unit 700. The X-ray radiation unit 700 radiates X-rays in an array manner. As illustrated in FIG. 7A, the X-ray radiation unit 700 includes an X-ray generation unit 710 in which an X-ray source is located with an arrayed mask 720 on an X-ray emitting side of the X-ray generation unit 710. Only masks corresponding to a target X-ray irradiation site are removed from the arrayed mask 720 to emit X-rays through the empty space of the arrayed mask 720 from which the mask is removed. FIG. 7B is a detailed view illustrating an example of the arrayed mask 720 disposed on the X-ray emitting side, which includes masks 720-1 to 720-7, including the leftmost mask 720-1 and the rightmost mask 720-7. For example, to radiate X-rays through a center region of the X-ray generation unit 710, only the mask 720-4 in the middle of the mask array 720 is removed. The other masks 720-1, 720-2, 720-3, 720-5, 720-6, and 720-7 remain to block X-rays. Taking the frequency and interval of X-ray radiations into account, the size of each mask is appropriately adjusted.

FIG. 8 is a diagram illustrating an example of variations in X-ray penetration distance in a target 810 when the X-ray radiation unit 530 of FIG. 5 is located at center and side points on an arc path 800. In this example, a cross-section of the target 810 is disposed on an X-ray detection unit 820. When the X-ray radiation unit 530 radiates X-rays in the center position G of the arc path 800, an X-ray penetration distance in the target 810, as indicated by "a", is shortest and perpendicular to the X-ray detection unit 820. Meanwhile, when the X-ray radiation unit 530 radiates X-rays in the side position H of the arc path 800 after being shifted from the center position G of the arc path 800 by α°, an X-ray penetration distance in the target 810, as indicated by "b", is longest and extends in an oblique direction with respect to the X-ray detection unit 820. X-rays have physical characteristics whereby, when a traveling path is relatively long, the absorption or scattering geometrically becomes relatively great. Thus, when the X-ray radiation unit 530 radiates a homogeneous spectrum of X-rays in the position G or H, the X-rays radiated in the position G may pass through the target 810 and be detected by the X-ray detection unit 820, while most of the X-rays radiated in the position H may fail to pass through the target 810.

In other words, in the case where the location of the X-ray radiation unit 530 is shifted within a predefined range, the X-ray penetration distance in the target may be increased. Due to the physical characteristics of X-rays described above whereby the longer traveling path of X-rays leads to geometrically increased absorption or scattering of the X-rays, a reduced number of photons may reach the X-ray detection unit.

In an example where tissue overlap is not experienced, according to tomosynthesis, images are captured of a plurality of tomograms at different angles with the X-ray radiation unit 530 being shifted to different positions within a predefined range. Herein, when the range of angles in which the X-ray radiation unit 530 is shifted is relatively great, an amount of information obtainable in a depth direction is relatively great.

In an example, one or more spectra of X-rays are used. A low-energy spectrum of X-rays with a low penetrating power but a high tissue-to-tissue contrast is used for a short X-ray penetration distance, and a high-energy spectrum of X-rays with a high penetrating power is used for a long X-ray penetration distance. This ensures a wider range of angles in which the X-ray radiation unit 530 may be shifted. If X-ray penetration distances in a target are not problematic, for example, if X-ray penetration distances in a target are within a range of distances by which two or more different spectra of X-rays can pass through, the two or more spectra of X-rays are repeatedly radiated in an alternating manner.

FIG. 9 is a flowchart illustrating an example of an X-ray imaging method. Even if not described below, any content described above in connection with the X-ray imaging apparatus may apply to the X-ray imaging method described below.

A target to undergo X-ray imaging is appropriately positioned (910). For example, referring to the examples illustrated in FIGS. 2 and 5, the target is placed at an appropriate location on the X-ray detection unit 250, 540 to await X-ray irradiation. The placed target is immobilized, using, for example, a press member 240, to restrict movement during imaging to attain accurate results.

The input unit 510 receives (920) a command to perform X-ray imaging from the user. The received command may be any command known to one of ordinary skill in the art to control the X-ray imaging apparatus 200, such as, for example, a command to shift the location of the X-ray radiation unit 270, 530, a command to radiate X-rays, a command to adjust a parameter to generate heterogeneous spectra of X-rays, a command to rotate the body of the X-ray imaging apparatus 200 or the X-ray radiation unit 270, 530, or a command to move the press unit 240 or the X-ray detection unit 250, 540.

The X-ray imaging apparatus 200 performs (930) an X-ray imaging mode, which is described with reference to FIG. 10. FIG. 10 is a detailed flowchart illustrating an example of an X-ray imaging mode, which corresponds to the performing of the X-ray imaging mode recited with respect to FIG. 9.

For example, the X-ray radiation unit 270, 530 radiates (1010) X-rays toward the target. If there has been a previous radiation of X-rays, the X-ray radiation unit 270, 530 may radiate at a location different from that of the previous radiation. A spectrum of X-rays different from that which was previously radiated may be radiated.

The X-ray detection unit 250, 540 detects (1020) the radiated X-rays that have passed through the target. The X-ray detection unit 250, 540 detects the radiated X-rays that have passed through the target and converts the detected X-rays into an electric signal.

The image data generation unit 550 generates (1030) cross-section data of the target that corresponds to the detected X-rays. The X-rays that have passed through the target after being radiated thereto reach the X-ray detection unit 250, 540, which then detects the X-rays, converts them into an electric signal with information about a cross-sectional layer of the target, and digitizes the electric signal to generate cross-section data. If multiple pieces of cross-section data are generated through several instances of X-ray radiation, 3D volume data to represent the target in three dimensions may be generated. The storage unit 560 stores (1040) the generated cross-section data or the 3D volume data.

A determination regarding a termination of a capturing of images by using X-rays is performed (940). In an example, it is determined whether the frequency of X-ray radiations performed is greater than a predetermined number that is large enough to secure generation of as many X-ray images as required. If the frequency of X-ray radiations performed is less than the predetermined number, i.e., is insufficient to terminate imaging with X-rays, the process returns to the performing (930) of the X-ray imaging mode.

If the frequency of X-ray radiations performed is greater than the predetermined number and sufficient to attain X-ray images for diagnosis, the output unit 570 outputs (950) an X-ray imaging result to an image processing apparatus. In an example, the X-ray imaging result is cross-section data to represent a cross-sectional layer of the target that is generated by the image data generation unit 550 or 3D volume data to represent the target in three dimensions. In this example, the cross-section or 3D volume data is stored in the storage unit 560. Further, the output unit 570 receives the cross-section or 3D volume data transferred from the storage unit 560 and outputs the cross-section or 3D volume data to the image processing apparatus.

The units described herein may be implemented using hardware components and software components, such as, for example, microphones, amplifiers, band-pass filters, audio to digital convertors, and processing devices. A processing device may be implemented using one or more general-purpose or special purpose computers, such as, for example, a processor, a controller and an arithmetic logic unit, a digital signal processor, a microcomputer, a field programmable array, a programmable logic unit, a microprocessor or any other device capable of responding to and executing instructions in a defined manner. The processing device may run an operating system (OS) and one or more software applications that run on the OS. The processing device also may access, store, manipulate, process, and create data in response to execution of the software. For purpose of simplicity, the description of a processing device is used as singular; however, one skilled in the art will appreciated that a processing device may include multiple processing elements and multiple types of processing elements. For example, a processing device may include multiple processors or a processor and a controller. In addition, different processing configurations are possible, such a parallel processors. As used herein, a processing device configured to implement a function A includes a processor programmed to run specific software. In addition, a processing device configured to implement a function A, a function B, and a function C may include configurations, such as, for example, a processor configured to implement both functions A, B, and C, a first processor configured to implement function A, and a second processor configured to implement functions B and C, a first processor to implement function A, a second processor configured to implement function B, and a third processor configured to implement function C, a first processor configured to implement function A, and a second processor configured to implement functions B and C, a first processor configured to implement functions A, B, C, and a second processor configured to implement functions A, B, and C, and so on.

The software may include a computer program, a piece of code, an instruction, or some combination thereof, for independently or collectively instructing or configuring the processing device to operate as desired. Software and data may be embodied permanently or temporarily in any type of machine, component, physical or virtual equipment, computer storage medium or device, or in a propagated signal wave capable of providing instructions or data to or being interpreted by the processing device. The software also may be distributed over network coupled computer systems so that the software is stored and executed in a distributed fashion. In particular, the software and data may be stored by one or more computer readable recording mediums. The computer readable recording medium may include any data storage device that can store data which can be thereafter read by a computer system or processing device. Examples of the computer readable recording medium include read-only memory (ROM), random-access memory (RAM), CD-ROMs, magnetic tapes, floppy disks, optical data storage devices. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein.

Program instructions to perform a method described herein, or one or more operations thereof, may be recorded, stored, or fixed in one or more computer-readable storage media. The program instructions may be implemented by a computer. For example, the computer may cause a processor to execute the program instructions. The media may include, alone or in combination with the program instructions, data files, data structures, and the like. Examples of computer-readable storage media include magnetic media, such as hard disks, floppy disks, and magnetic tape; optical media such as CD ROM disks and DVDs; magneto-optical media, such as optical disks; and hardware devices that are specially configured to store and perform program instructions, such as read-only memory (ROM), random access memory (RAM), flash memory, and the like. Examples of program instructions include machine code, such as produced by a compiler, and files containing higher level code that may be executed by the computer using an interpreter. The program instructions, that is, software, may be distributed over network coupled computer systems so that the software is stored and executed in a distributed fashion. For example, the software and data may be stored by one or more computer readable storage mediums. Also, functional programs, codes, and code segments for accomplishing the example embodiments disclosed herein can be easily construed by programmers skilled in the art to which the embodiments pertain based on and using the flow diagrams and block diagrams of the figures and their corresponding descriptions as provided herein. Also, the described units to perform an operation or a method may be hardware, software, or some combination of hardware and software. For example, the unit may be a software package running on a computer or the computer on which that software is running.

A number of examples have been described above. Nevertheless, it will be understood that various modifications may be made. For example, suitable results may be achieved if the described techniques are performed in a different order and/or if components in a described system, architecture, device, or circuit are combined in a different manner and/or replaced or supplemented by other components or their equivalents. Accordingly, other implementations are within the scope of the following claims.

What is claimed is:

1. An X-ray imaging apparatus, comprising:
an X-ray radiation unit configured to radiate a first X-ray and a second X-ray onto a target along a predetermined path;
an X-ray detection unit configured to detect the radiated first X-ray and the second X-ray that have passed through the target; and
an image data generation unit configured to generate cross-section data that respectively corresponds to the detected first X-ray and the detected second X-ray and represents a predetermined cross-sectional layer of the target,
wherein the first X-ray is radiated at a location on the predetermined path that is different from a location on the predetermined path at which the second X-ray is radiated, the first X-ray comprising X-ray spectra that are different from X-ray spectra of the second X-ray.

2. The X-ray imaging apparatus of claim 1, wherein the X-ray spectra of the first X-ray and the X-ray spectra of the second X-ray are respectively dependent on the locations in which the first X-ray and the second X-ray are radiated by the X-ray radiation unit.

3. The X-ray imaging apparatus of claim 1, wherein the X-ray radiation unit comprises an X-ray generation unit and an arrayed mask, the X-ray generation unit being configured to radiate the first X-ray and the second X-ray onto the target, the arrayed mask being on an X-ray emitting side of the X-ray generation unit, the arrayed mask comprising masks that are removable based on a site at which the target is disposed and the locations at which the first X-ray and the second X-ray are disposed.

4. The X-ray imaging apparatus of claim 1, wherein the X-ray radiation unit is further configured to radiate one or more spectra of X-rays at a location on the predetermined path that is different from a location on the predetermined path at which the first X-ray and the second X-ray are radiated, the one or more spectra being different from the spectra of the first X-ray and the second X-ray.

5. The X-ray imaging apparatus of claim 1, wherein the first X-ray has an energy spectrum that is greater than an energy spectrum of the second X-ray when the location at which the first X-ray is radiated is farther away from a center of the predetermined path than the location at which the second X-ray is radiated, and wherein the energy spectrum of the second X-ray is greater than the energy spectrum of the first X-ray when the location at which the second X-ray is radiated is farther away from the center of the predetermined path than the location at which the first X-ray is radiated.

6. The X-ray imaging apparatus of claim 1, wherein the first X-ray and the second X-ray are alternately radiated at different locations on the predetermined path.

7. The X-ray imaging apparatus of claim 1, wherein, when multiple pieces of cross-section data are generated based on multiple radiations of X-rays by the X-ray radiation unit in multiple locations, the image data generation unit is further configured to generate three-dimensional (3D) volume data representing the target in three dimensions by cumulating the generated multiple pieces of cross-section data.

8. The X-ray imaging apparatus of claim 1, further comprising:
a storage unit configured to store the generated cross-section data.

9. The X-ray imaging apparatus of claim 1, wherein the X-ray imaging apparatus is used in tomosynthesis.

10. An X-ray imaging method, comprising:
radiating a first X-ray and a second X-ray onto a target along a predetermined path;
detecting the radiated first X-ray and the radiated second X-ray that have passed through the target; and
generating cross-section data that respectively corresponds to the detected first X-ray and the detected second X-ray and represents a predetermined cross-sectional layer of the target,
wherein the first X-ray is radiated at a location on the predetermined path that is different from a location on the predetermined path at which the second X-ray is radiated, the first X-ray comprising X-ray spectra that are different from X-ray spectra of the second X-ray.

11. The method of claim 10, wherein the X-ray spectra of the first X-ray and the X-ray spectra of the second X-ray are respectively dependent on the locations in which the first X-ray and the second X-ray are radiated.

12. The method of claim 10, wherein the radiating of the first X-ray and the second X-ray comprises radiating one or more spectra of X-rays at a location on the predetermined path that is different from a location on the predetermined path at which the first X-ray and the second X-ray are radiated, the one or more spectra being different from the spectra of the first X-ray and the second X-ray.

13. The method of claim 10, wherein the first X-ray has an energy spectrum that is greater than an energy spectrum of the second X-ray when the location at which the first X-ray is radiated is farther away from a center of the predetermined path than the location at which the second X-ray is radiated, and wherein the energy spectrum of the second X-ray is greater than the energy spectrum of the first X-ray when the location at which the second X-ray is radiated is farther away from the center of the predetermined path than the location at which the first X-ray is radiated.

14. The method of claim 10, wherein the first X-ray and the second X-ray are alternately radiated at different locations on the predetermined path.

15. The method of claim 10, further comprising, when multiple pieces of cross-section data are generated based on multiple radiations of X-rays in multiple locations:
generating three-dimensional (3D) volume data representing the target in three dimensions by cumulating the generated multiple pieces of cross-section data.

16. The method of claim 10, further comprising:
storing the generated cross-section data.

17. The method of claim 10, wherein the X-ray imaging method is used in tomosynthesis.

18. A non-transitory computer readable recording medium having recorded thereon a program for executing the method of claim 10.

19. An X-ray imaging apparatus, comprising:
an X-ray radiation unit configured to radiate X-rays onto a target from one or more locations along a predetermined path, each of the radiated X-rays comprising a respective X-ray spectra corresponding to the locations, respectively;
an X-ray detection unit configured to detect a plurality of the radiated X-rays that have passed through the target;
an image data generation unit configured to generate pieces of cross-section data and three-dimensional (3D) volume data, the 3D volume data being configured to represent the target in three dimensions, the pieces respectively corresponding to the detected plurality of the radiated X-rays and representing predetermined cross-sectional layers of the target, the pieces being configured to cumulatively represent the target in three dimensions as the 3D volume data.

* * * * *